United States Patent [19]
Santus et al.

[11] Patent Number: 5,883,115
[45] Date of Patent: Mar. 16, 1999

[54] TRANSDERMAL DELIVERY OF THE EUTOMER OF A CHIRAL DRUG

[75] Inventors: G. Carlo Santus, Milan, Italy; Richard W. Baker, Palo Alto, Calif.

[73] Assignee: Pharmetrix Division Technical Chemicals & Products, Inc., Menlo Park, Calif.

[21] Appl. No.: 148,704

[22] Filed: Nov. 8, 1993

Related U.S. Application Data

[63] Continuation-in-part of Ser. No. 973,801, Nov. 9, 1992, abandoned.

[51] Int. Cl.$^6$ ............... A61K 31/40; A61K 31/35; A61K 31/16; A61K 31/135
[52] U.S. Cl. ............... 514/413; 514/457; 514/626; 514/648; 514/654; 514/947; 424/449; 424/486
[58] Field of Search ............... 514/413, 457, 514/626, 648, 654, 947; 424/449, 486

[56] References Cited

U.S. PATENT DOCUMENTS

| | | | |
|---|---|---|---|
| 4,089,969 | 5/1978 | Muchowski et al. | 424/274 |
| 4,668,232 | 5/1987 | Cordes et al. | 604/897 |
| 4,690,683 | 9/1987 | Chien et al. | 604/896 |
| 4,818,541 | 4/1989 | Sanderson | 424/448 |
| 4,822,617 | 4/1989 | Panoz | 424/449 |
| 4,927,854 | 5/1990 | Sunshine et al. | 514/570 |
| 4,940,586 | 7/1990 | Cheng et al. | 424/464 |
| 4,940,761 | 7/1990 | Davis | 514/179 |
| 4,983,395 | 1/1991 | Chang et al. | 424/448 |
| 4,992,445 | 2/1991 | Lawter et al. | 514/279 |
| 5,049,386 | 9/1991 | Eppstein et al. | 424/427 |
| 5,091,182 | 2/1992 | Ong et al. | 424/400 |
| 5,114,946 | 5/1992 | Lawter et al. | 514/279 |
| 5,124,157 | 6/1992 | Colley et al. | 424/448 |
| 5,132,119 | 7/1992 | Lee | 424/646 |
| 5,304,379 | 4/1994 | Cormier et al. | 424/449 |

OTHER PUBLICATIONS

Stinson, S.C., "Chiral Drugs" *C&EN* pp. 46–79 (Sep. 28, 1992).
Knadler, M.P., et al. (1992) "Stereoselective Disposition of Flurbiprofen in Normal Volunteers" *Br. J. Clin. Pharmac.* 33:369–375.
Mroszczak, E., et al. (1991) *Clin. Pharmacology & Therapeutics* 49:126.
Campbell, D.B. (1990) "Stereoselectivity in Clinical Pharmacokinetics and Drug Development" *European Journal of Drug Metabolism and Pharmacokinetics* 15(2):109–125.
Rowland, M., et al. (1989) *Clinical Pharmacokinetics: Concepts and Applications*, 2nd Ed. pp. 19–25.
Smith, D.F. (1989) "The Stereoselectivity of Drug Action" *Pharmacology & Taxicology* 65:321–331.
Jamali, F., et al. (1989) "Enantioselectivity Aspects of Drug Action and Disposition: Therapeutic Pitfalls" *Journal of Pharmaceutical Sciences* 78(9):695–714.
Ariens, E.J., et al. "Stereoselectivity of Bioactive Xenobiotics" *Biochemical Pharmacology* 37(1):9–18, 1989.
Guzman, A., et al. (1986) "Absolute Configuration of (–)-5-Benzoyl-1,2-dihydro-3H-pyrrolo[1,2-a]pyrrole-1-carboxylicAcid the Active Enantiomer of Ketorolac" *J. Med. Chem.* 29:589–591.
Drayer, D.E. (1986) "Pharmacodynamic and Pharmacokinetic Differences Between Drug Enantiomers in Humans: An Overview" *Clinical Pharmacology & Therapeutics* 40(2):125–133.
Baker, R. (1987) *Controlled Release of Biologically Active Agents*, John Wiley & Sons, New York, pp. 4–10.

*Primary Examiner*—William R. A. Jarvis
*Attorney, Agent, or Firm*—Peter J. Manso

[57] ABSTRACT

A pharmaceutical composition of the eutomer of a chiral drug is disclosed whereby the eutomer has a clearance value greater than that of the racemic mixture of the chiral drug. The pharmaceutical compositions of the present invention allow the delivery of therapeutically effective levels of drugs at doses much lower than would be required when the drug is delivered by conventional injection methods.

8 Claims, 3 Drawing Sheets

TRANSDERMAL DELIVERY OF THE EUTOMER OF A CHIRAL DRUG

CROSS REFERENCE TO RELATED APPLICATIONS

The present application is a continuation-in-part of U.S. Ser. No. 07/973,801 filed Nov. 9, 1992, now abandoned, the contents of which are hereby incorporated by reference.

FIELD OF THE INVENTION

The present invention is directed to the transdermal delivery of the eutomer of a chiral drug. More particularly, the invention is related to the method of transdermal delivery of a eutomer of a chiral drug when the eutomer has greater clearance and pharmacodynamic activity than the racemic mixture of the chiral drug.

BACKGROUND OF THE INVENTION

When a drug is administered intravenously or orally, the initial level of drug in the blood rapidly rises to a maximum. This initial level of drug is generally much higher than the therapeutically effective level. For example, FIG. 1 shows that sometimes initial levels of drugs administered orally may reach toxic concentrations resulting in undesirable side-effects. This is known as "overdosing." After the drug is administered and rises to a maximum level in the blood, the level then falls slowly as the drug is distributed, metabolized, excreted, or degraded. Eventually, the level of drug in the blood falls below the therapeutically effective level (i.e., there is "underdosing"). At this point, the drug needs to be re-administered to achieve effectiveness. Maintaining the concentration of drug in the blood between the minimum therapeutically effective level and toxic levels is important. One way to achieve this is to administer lower drug doses to the patient more frequently. This, however, is an unacceptable alternative in most instances.

Transdermal delivery of drugs offers a means of circumventing the problems of overdosing and underdosing that are associated with conventional drug delivery methods. The transdermal delivery of drugs can be designed so that the rate of delivery of the drug closely follows the rate of the clearance of the drug from the environment, thus keeping constant levels of drug in the blood, and reducing drug waste and overdosing problems. FIG. 1 displays the blood levels from transdermal and conventional oral delivery of drugs over a period of time.

In addition to the advantage of being able to control drug delivery rates, transdermal drug delivery also provides a comfortable, convenient and noninvasive way of administering drugs. Gastrointestinal irritation and other side-effects, often associated with oral drug delivery, are eliminated.

However, the amount of drug that can be delivered to a patient transdermally has limitations. Many drugs are poor candidates for transdermal delivery due to limitations on the permeability of the drug through the skin, or the large dose of the drug required for therapeutic efficacy. A partial solution to the dose problem associated with transdermal delivery can be employed when the drug to be delivered is a racemic mixture and most or all of the biological activity of the drug is associated with one enantiomer of the drug.

Delivery of eutomers rather than racemic mixtures to reduce the dose of drug to be delivered is known. For example, the drug Naproxen is manufactured as the racemic mixture and then resolved and sold to patients as the eutomer to reduce the size of the tablets to be used from 1000 mg tablets for the racemic drug to a more practical 500 mg tablets for the eutomer. The maximum reduction in dose that can be achieved when the eutomer is used is 50% since the racemic mixture consists of a 50:50 mixture of the two enantiomers.

Accordingly, it is an object of this invention to provide a pharmaceutical composition for the transdermal delivery of the eutomer of a chiral drug where the clearance value of the eutomer is greater than that of the racemic mixture.

It is another object of this invention to provide a transdermal patch for the delivery of S(−) ketorolac.

These and other objects and features of the invention will be apparent to those skilled in the art from the following detailed description and appended claims when taken in conjunction with the figures.

SUMMARY OF THE INVENTION

A pharmaceutical composition of a chiral drug is described comprising the eutomer of the chiral drug which has a clearance value greater than that of the racemic mixture of the chiral drug and a vehicle for the transdermal delivery of the eutomer. In a preferred embodiment, the chiral drug is ketorolac.

A method for administering the above pharmaceutical compositions is also disclosed.

DETAILED DESCRIPTION OF THE INVENTION

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the foregoing terms are defined below.

The term "therapeutically effective level" as used herein refers to the minimal blood level of drug required to achieve a therapeutic effect.

The term "pharmacodynamic activity" as used herein refers to the biochemical and physiological effect of drugs.

The term "eutomer" or "active enantiomer" as used herein refers to the stereoisomer of a chiral drug that exhibits greater pharmacodynamic activity than its counterpart stereoisomer. When reference is made to the term "eutomer" it is meant also to include the substantially pure eutomer which may also contain very small amounts of the other enantiomer.

The term "distomer" or "inactive enantiomer" as used herein refers to the stereoisomer of a chiral drug that exhibits lower pharmacodynamic activity than its counterpart stereoisomer.

The term "eudismic ratio" as used herein refers to the ratio of pharmacodynamic activity between the eutomer and the distomer. A eudismic ratio of one indicates that the two enantiomers have the same pharmacodynamic activity for any particular therapeutic purpose. Thus, eudismic ratios of greater than one indicate that the eutomer has a greater pharmacodynamic activity than the distomer.

The term "clearance" as used herein refers to the rate of removal of a drug from the body expressed as the in vivo volume equivalent of the substance being removed per unit time. The concept of clearance is described in detail in Rowland & Tozer's, *Clinical Pharmacokinetics: Concepts and Applications,* (2nd Ed. 1989), which is hereby incorporated by reference. Clearance does not indicate how much drug is being removed from the system but, rather, the volume of biological fluid such as blood or plasma that would have to be completely freed of drug to account for the elimination. Clearance is expressed as a volume per unit of time. Clearance by means of various organs of elimination is additive. Elimination of drug may occur as a result of processes that occur in the kidney, liver, and other organs. When the respective clearance by each organ is added together, they equal total systemic clearance.

The term "clearance ratio" as used herein refers to the ratio of the clearance value of the eutomer to the clearance value of the racemic mixture.

The term "half-life" as used herein refers to the amount of time it takes the total level of drug in a body to decrease by 50%.

The term "vehicle for transdermal delivery" as used herein refers to any means used for the transdermal delivery of drugs including, but not limited to, creams, lotions, ointments, gels, pastes, bandages and patches.

The term "injectable dose equivalent" as used herein refers to the amount of drug required when delivered transdermally to achieve the same therapeutic effect as a specified injectable dose of drug.

The term "ketorolac" as used herein refers to any therapeutic form of the analgesic ketorolac including but not limited to its pharmaceutically effective salts and ketorolac tromethamine.

DESCRIPTION OF THE PREFERRED EMBODIMENTS

Certain chiral drugs such as ketorolac may be considered marginal or poor candidates for transdermal delivery even if the resolved pure active form of the drug is used due to the large dose required to achieve a therapeutic effect (above 20–30 mg/day). However, the Applicants have discovered that significantly less drug may be needed to achieve a therapeutically effective blood level when the drug is transdermally delivered as the eutomer. This appears to be the case when the eutomer of the drug has a shorter half-life or a greater clearance than the racemic mixture (racemate) of the drug.

Conversely, and also unexpectedly, some drugs which may appear to be good candidates for transdermal delivery based on the clearance of the racemic mixture and the known non-transdermal 24-hour dose do not achieve the required therapeutic effect when the calculated transdermal dose of the eutomer is delivered. That is, the administration of the eutomer of some drugs, rather than the racemate, requires the administration of more drug than previously suggested. This unexpectedly poor result occurs when the eutomer of the drug has a longer half-life or lower clearance than the racemic mixture of the drug.

Thus, by determining the dose of the active form of a drug according to the method of the present invention, a more carefully targeted amount of a drug can be transdermally delivered to a patient, thus minimizing the problems associated with underdosing or overdosing.

Oftentimes the required dose of a drug when delivered transdermally can be one half or less that of the dose delivered by non-transdermal routes of administration, such as intravenous or oral. This is particularly true if the drug has a high clearance value. For non-transdermal drug delivery methods, if a drug has a high clearance value it is necessary to administer a large dose of drug to maintain the plasma serum concentration of the drug at therapeutically effective levels for as long as possible. But, with transdermal delivery, the dose of a drug with a high clearance value can be lower since the drug can be released at a controlled rate, and does not have to be administered at levels much greater than the therapeutically effective level.

The half-life of a drug is the amount of time it takes the total level of drug in a body to decrease by 50%. Clearance is related to the half-life of a drug by Equation 1:

$$T_{1/2} = \frac{0.693 \times \text{Volume of distribution}}{\text{Clearance}} \qquad (1)$$

The relationship between the conventional dose of a drug and the dose of drug delivered transdermally can be calculated if the half-life of the drug is known. This procedure is described on pages 5–10 of Baker, R. W., *Controlled Release of Biologically Active Agents,* John Wiley and Sons, New York, (1987), [hereinafter Baker], the contents of which are hereby incorporated by reference.

Figure 1:
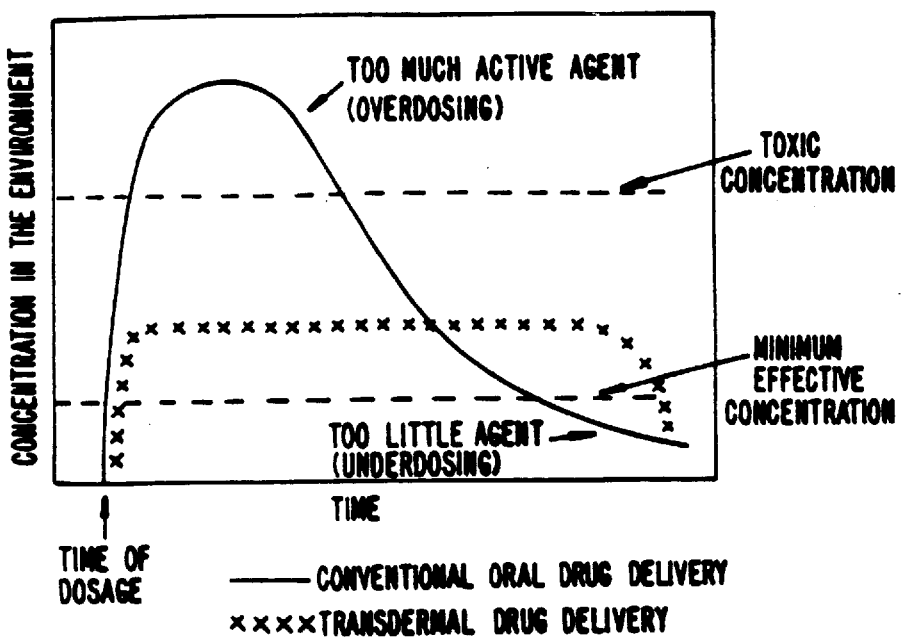
FIG. 1 compares the levels of drug in a system after conventional oral delivery and transdermal delivery.
Figure 2:
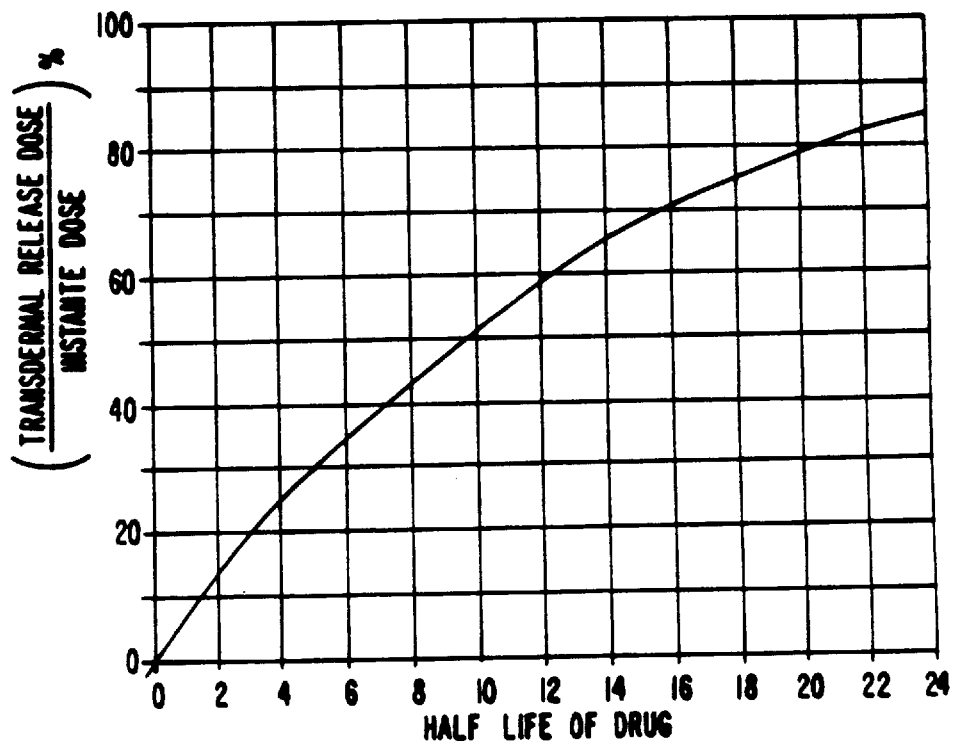
FIG. 2 compares the ratio of drug delivered transdermally (controlled release) to the drug delivered as an instant dose (drug injection) required to achieve 24 hour therapy as a function of the half-life of the drug.

FIG. 2 is a graphical illustration of the relationship between the conventional dose of a drug and the dose of drug delivered transdermally, where the half life of the drug is known. For example, the x-axis of FIG. 2 represents the half life of the drug in question. The point on the y-axis corresponding to that half life is the % ratio between the transdermal release dose and the instant dose of the drug. The instant dose refers to a dosage that is not a controlled release dosage. The most common instant dosage is an intravenous dose. Intramuscular or oral doses are also instant doses, although the blood levels of the drug are subject to an initial delay which varies depending on the half-life of the drug, the method of formulation and the route of administration of the drug.

As noted from the shape of the curve in FIG. 2, as the half life of a drug increases, the amount required to be delivered transdermally approaches that required by routes of administration that are not rate-controlled. Illustrations of this relationship between the non-transdermal and the transdermal dose are provided in Table I. Thus, if the half-life of the drug is 24 hours, then a transdermal patch delivering drug to the body at a relatively constant rate should only have to deliver 84.5% of the dose of a conventional instant dose form of the drug delivered once every 24 hours. In this case, the advantage offered by controlled transdermal delivery is relatively small, only a 15.5% reduction in dose. However, if the half-life of the drug is 3 hours, for example, then the advantage offered by transdermal delivery is much greater compared to conventional delivery once every 24 hours, namely a reduction in dose of almost 80%.

TABLE I

| Drug Half-life (in hours) | Ratio of dose required of controlled release form compared to conventional form (for a 24-hour device) |
|---|---|
| 24 | 0.845 |
| 12 | 0.595 |
| 6 | 0.350 |
| 3 | 0.205 |

Despite the advantages of delivering drugs with high clearance values and low half-lives transdermally, there are still limitations to transdermal drug delivery. For instance, it is difficult to deliver drugs transdermally at high doses. Typically 20–30 mg/day is the upper limit of practical transdermal drug delivery, due to the limited permeability of the stratum corneum layer of the skin. At doses exceeding 20–30 mg/day, either an extremely large patch is needed or a very permeable drug.

Patch size is a significant factor in the design and ultimate acceptance of transdermal patches. Various contact-related side effects are associated with patches including allergies, skin irritation, rashes and removal of hair follicles. Minimizing the patch size minimizes the skin area which may suffer from these side effects. In addition, the size of the patch is important to patients from the point of aesthetics, comfort, and wearability. In one survey of nitroglycerin patches, no patient considered any tested patch to be too small, and patches of 33 $cm^2$ and 57 $cm^2$ were considered too large, Rayment et al, *Comparative acceptance of three transdermal nitroglycerin placebo patches,* Am. J. of Hospital Pharmacy (1985) 42: 1362, and Gatlin, *Comparative patient preference for two transdermal nitroglycerin patches,* (1985) Curr. Therapeutic Res. 38(5): 733.

Currently marketed transdermal patches are described in Gurny, et al. *Dermal and Transdermal Drug Delivery: New Insights and Perspectives,* Proceedings of the Second International Symposium of the Association for Pharmaceutical Technology (1991), at page 25, the contents of which are hereby incorporated by reference. Transdermal patches described in Gurny have an upper dosage range on the order of 15 mg/day (nitroglycerine) and of 21 mg per day (nicotine) of drug delivered. Both of these drugs are very permeable. The patch size active area of the patches described in Gurny ranges up to 40 $cm^2$, with a total patch area ranging as high as 93 $cm^2$. Thus, there are permeability and patient-related constraints for the transdermal delivery of drugs that require high doses for therapeutic efficacy.

As a result, many drugs that should benefit from the controlled release conferred by a transdermal delivery means are not used because the dose required is greater than 20–30 mg/day. This is demonstrated with the analgesic ketorolac. A typical 24 hour dose of ketorolac delivered by injection is approximately 200 mg. It can be shown that approximately 100 mg of the eutomer of ketorolac when delivered by injection achieves the same biological effect. However, the expected transdermal dose of ketorolac based on the published half-life of this drug of approximately 4 hours is about 25 mg if the active form of the drug is used, or about 50 mg of drug if the racemate is used. In this particular case, one would expect that using the active form of the drug would bring the dose of the drug required to the upper end of that achievable with transdermal delivery (20–30 mg/day); but the active area of the patch required would still be rather large, on the order of 20 to 50 $cm^2$, perhaps larger.

An area of drug delivery that is receiving increased attention is the implication of stereochemistry in drug action and disposition. While 25% of all drugs that are used are chiral molecules, approximately 80% of these are used as racemic mixtures. That is, they exist as mixtures of two stereoisomers, or enantiomers, whose molecules are nonsuperimposable mirror images of one another. The enantiomers are typically designated as either (+) and (−) or as (d) and (l), which denotes optical rotation at the chiral center. Stereoisomerism may also be denoted as (D) or (L) or as (R) and (S) forms, which are descriptors of absolute configuration. The (+) and (−) drug enantiomers may have varying pharmacodynamic properties due to the stereoselectivity of drug action. Either the (+) or the (−) form may be the pharmacologically more active form, depending on the drug and the particular activity being measured.

Recently, more attention has been given to these differences in efforts to improve drug delivery methods. For example, improved flux rates in the transdermal delivery of individual enantiomers of phenylpropanolamine have been demonstrated as compared to the racemic mixture in U.S. Pat. No. 4,818,541 (Sanderson). Improved flux rates of the transdermal delivery of individual enantiomers of chiral drugs has been shown when the racemic mixture of the drug has a higher melting point than that of the enantiomer in U.S. Pat. No. 5,225,946 (Lawter et al.). Various articles describe the different characteristics that the individual enantiomers of a chiral drug may exhibit. For example, see Jamali et al., J. of Pharmaceutical Sciences 78: 695–714 (1989) and D. B. Campbell, European J. of Drug Metabolism and Pharmacokinetics 15: 109–125 (1990).

Enantiomers may have different therapeutic effects from each other or from the racemic mixture. One enantiomer may have pharmacodynamic activity that is greater than the other enantiomer. The enantiomer with the greater therapeutic activity for the desired purpose is referred to as the "active enantiomer" or "eutomer" and the one with less activity is referred to as the "inactive enantiomer" (although it may exhibit some activity) or "distomer". The ratio of pharmacodynamic activity between the eutomer and the distomer is called the "eudismic ratio." Table II lists the eudismic ratio of various chiral drugs.

TABLE II

| Drug Class | Eutomer | Eudismic Ratio | Pharmacodynamic Activity |
|---|---|---|---|
| β agonist | (−) Terbutaline | 3000 | Smooth muscle relaxation |
| Antidepressant | S(+) Oxaprotiline | 1000 | NA uptake inhibition |
| Antimuscarinic | S(+) Bethanecol | 800 | Muscle contraction |
| Antipsychotic | (+) Butaclamol | 300 | Behavioral |
| β antagonist | S(−) Pindolol | 200 | Isoprenaline inhibition |
| Analgesic | (−) Ketorolac | 230 | Prostaglandin Inhibition |
| Muscle relaxant | R(−) Baclofen | 100 | Nerve Transmission Block |
| Opiate antagonist | R(−) Methadone | 30 | Receptor binding |
| Benzodiazepine | (+) Camazepam | 14 | Receptor binding |
| Antagonist | (+) Amosulolol | 10 | Receptor binding |
| Calcium Blocker | (−) Verapamil | 8 | Receptor binding |
| Anticoagulant | S(−) Warfarin | 5 | Anticoagulant |

TABLE II-continued

| Drug Class | Eutomer | Eudismic Ratio | Pharmacodynamic Activity |
|---|---|---|---|
| Antiobesity | S(+) Fenfluramine | 4 | Food intake reduction |
| Anaesthetic | S(+) Ketamine | 3 | Anaesthesia |
| Antianythmic | R(−) Tocainide | 3 | Antiarrythmic |
| Antidepressant | (+)&(−) Fluoxetine | 1 | 5HT uptake blockade |

When the eutomer of a chiral drug is purified or resolved from its racemic mixture, the therapeutically effective dose is, by definition, less than that of the racemate, for any particular therapeutic purpose. The biological effect of a racemate can be defined as the dose multiplied by the biological activity of the drug. For a racemic drug, where the two enantiomers are present in equal amounts, the biological effect is described by Equation 2:

$$\text{Biological effect of racemate} = \frac{D_R}{2} \times (a + b) \quad (2)$$

where "$D_R$" is the dose of the racemate administered, "a" is the activity of the eutomer, and "b" is the activity of the distomer. The biological effect of the eutomer, when delivered alone, can be defined as $D_E(a)$ where $D_E$ is the dose of the eutomer delivered. Thus, the dose of a eutomer required to achieve the same effect as an equivalent dose of a racemate can be calculated by Equation 3:

$$\frac{D_R}{2} \times (a + b) = D_E(a) \quad (3)$$

Thus, the ratio of the dose of the eutomer necessary to achieve the same biological effect as a dose of the racemate is calculated by solving Equation 3 to create Equation 4:

$$\frac{D_E}{D_R} = \frac{a+b}{2a} \times 100\% \quad (4)$$

$$= 0.5 \left(1 + \frac{1}{E.R.}\right) \times 100\%$$

where E.R. is the eudismic ratio. Thus, if the eudismic ratio is 10 (i.e., the eutomer is 10 times more active than the distomer), then the dose of the eutomer required to achieve the same biological effect as a dose of the racemate is only 55% of the dose of the racemate.

Table III provides examples of the calculation according to Equation 3 for chiral drugs with different eudismic ratios. As can be seen from Table III, administering the eutomer of a chiral drug can result in up to a 50% decrease in the effective drug dose. Decreases of greater than 50% are not expected, since the racemate is usually a 50:50 mixture of the two enantiomers.

TABLE III

| Eudismic Ratio | Dose of eutomer required to achieve effect of racemic mixture (in % dose of racemic mixture) |
|---|---|
| 1 | 100 |
| 2 | 75 |
| 5 | 60 |
| 10 | 55 |
| 50 | 51 |
| ∞ | 50 |

The method of using Equation 4 in screening potential candidate drugs for transdermal delivery is as follows. Using the dose of the racemic drug used to achieve 24 hour therapy, preferably the instant injectable dose of the drug, and the published half-life of the racemic drug, the expected dose of the racemic drug required for transdermal delivery is calculated. The data required for this type of calculation is found in compendiums such as Martindale, *Extra Pharmacopeia* J. E. F. Reynold (Ed.), Pharmaceutical Press and the references therein. The calculation procedure is described in page 5–10 of Baker (supra), and is exemplified in FIG. 2 and Table I.

The benefit to be expected by the use of the eutomer form of the drug is then determined by using Equation 4. The data in Table III shows the maximum benefit of using the eutomer is expected to be 50%.

However, the applicants have discovered that in certain cases, the dose needed of the eutomer of a chiral drug, when delivered transdermally, is actually less than 50% of the dose expected of the racemic mixture. In some instance, the transdermal dose required can be even less than 30%. It has been found that this is the case when the eutomer of a chiral drug has a greater clearance value than the racemic mixture. Thus, using the eutomer not only achieves the benefit described in Table 2, but unexpectedly even less drug is required if the drug is delivered transdermally. Thus the present invention allows for transdermal delivery of the active form of a drug in dosages less than would have been expected based on previous dosage calculations. Therefore, the use of transdermal drug delivery methods are particularly beneficial when the eutomer of a drug is delivered and when the clearance value of the eutomer is greater than that of the distomer or racemate.

Table IV shows the clearance ratio of various drugs where the clearance ratio is the ratio of the clearance of the eutomer to the clearance value of the racemic mixture. Clearance values of chiral drugs are available in the art. Generally, methods of determining clearance values are described in Rowland & Tozer, supra, and Goodman & Gilman's The *Pharmacological Basis of Therapeutics*, (8th ed. 1990).

TABLE IV

| Class | Drug | Clearance Ratio | Eudismic Ratio |
|---|---|---|---|
| Anticoagulant | S(−) Warfarin | 1.2 | 5 |
| Antiarrhythmic | R(−) Tocainide | 1.35 | 3 |
| Ca$^{++}$ channel-blocker | S(−) Verapamil | 1.4 | 8 |
| Antiarrhythmic | S(+) Disopyramide | 1.4 | 4 |
| Narcotic analgesic | R(−) Methadone | 1.5 | 30 |
| Analgesic | S(−) Ketorolac | 1.75 | 230 |
| Betablocker | S(−) Propranolol | 0.91 | |
| Anticoagulant | S(−) Phenprocoumon | 0.87 | 5 |
| Ca$^{++}$ channel-blocker | (+) Nilvadipine | 0.5 | 100 |
| Anaesthetic | S(+) Prilocaine | 0.25 | |
| Hypnotic | S(+) Hexobarbital | 0.20 | |
| Anticoagulant | R(+) Acenocoumarol | 0.13 | |

Table IV indicates that drugs can be grouped into two classes: one where the eutomers have clearance values greater than the racemic mixtures and thus have clearance ratios greater than one (drugs listed above the double line) and one where the eutomers have clearance values less than the racemic mixtures and thus have clearance ratios of less than one (drugs listed below the double line). The grouping of drugs into two classes based on clearance ratios assists in the calculation of the required transdermal dose according to the present invention. Drugs with clearance ratios of greater than 1 are indicated as likely candidate drugs, because the eutomer will have a greater clearance from the body than the racemic mixture. As noted from the relationship in Equation 1, half life and clearance are related. Thus, the eutomer with rapid clearance will have a correspondingly short half life, indicating that it may be a good candidate for the reduction in dose obtained by transdermal delivery means.

The present invention may be further described by way of example. As can be seen from Table IV, ketorolac falls within the first class of drugs described above, namely, having a clearance ratio greater than 1.

If the relative clearance ratio of the enantiomers of ketorolac was not considered, it would be expected from Equation 4 that the reduction in dose of the (−) enantiomer of ketorolac required to achieve a therapeutic effect equivalent to that of the racemic mixture is:

$$\frac{D_E}{D_R} = 0.5\left(1 + \frac{1}{230}\right) \times 100\%$$
$$= 50.2\%$$

Although marketed as a racemic mixture, it has been shown that essentially all of the pharmacological activity of ketorolac resides in the S(−) enantiomer. [Guzman et al., *J. Med. Chem.* 29: 598–591 (1986)]. Pharmacokinetic studies of the (−) and (+) enantiomers have shown that the clearance value of the (−) enantiomer is greater than that of the (+) enantiomer. [Mroszczak et al. *Clin Pharmacology & Therapeutics* 49:126 (1991)].

The conventional once per day injectable dose of ketorolac is approximately 200 mg/day. The half-life of the drug is about 4 hours. The delivery of the drug transdermally means that the dose can be reduced. The normal transdermal dose of racemic ketorolac required to achieve a therapeutic effect is expected to be 50 mg/day, based on the calculation From FIG. 2 and Table I. Thus, according to Equation 4, as applied above, only 50.2%, or 25.2 mg/day of the (−) form would be required to achieve the same effect. This dosage, borders on being too high for efficient transdermal drug delivery.

The applicants have discovered that surprisingly, the dose of the (−) form of ketorolac required to achieve an equivalent therapeutic effect can be even further reduced by a factor of about 1.75 due to the enantiomeric clearance ratio shown in Table IV, which is shown to be 1.75. In mathematical terms, the effect of the clearance ratio shown in Table IV on the dose of drug required to achieve a biological effect can be expressed by a modification of Equation 4 as shown by Equation 5:

$$\frac{D_E}{D_R} = 0.5\left(1 + \frac{1}{E.R.}\right) \times \frac{100\%}{C.R.} \qquad (5)$$

where C.R. is the clearance ratio of eutomer to racemate. Thus, the transdermal dose of ketorolac (−) enantiomer required to achieve a therapeutic effect equivalent to 200 mg/day of a racemic mixture delivered by conventional injection methods is only about 14.3 mg/day. Thus, by using Equation 5, the required transdermal dose of (−) ketorolac according to the present invention can be determined as follows:

$$\frac{D_E}{50} = 0.5\left(1 + \frac{1}{230}\right)\left(\frac{100\%}{1.75}\right) = 14.3 \text{ mg}$$

In other words, the injectable dose equivalent of 200 mg/day of racemic ketorolac is about 14.3 mg/day when delivered as the eutomer transdermally. This drug dosage falls within the range that can be efficiently delivered transdermally. Thus, the high clearance value of the eutomer of ketorolac requires that high doses of the drug be delivered by conventional drug delivery methods so that blood levels stay above the therapeutically effective level for a sufficient duration. The use of transdermal delivery methods can be used to an advantage to avoid drug waste and toxicity problems. Thus, ketorolac illustrates that a relatively low dosage is needed for the transdermal delivery of the eutomer of a chiral drug that has a greater clearance value than the distomer.

The approximate 40% reduction in transdermal dose that the applicants have discovered for ketorolac (that is, from 25.2 mgs/day to 14.3 mgs/day) is of considerable importance to designers of transdermal delivery systems. The reduced dose means that the patch size required to achieve a biological effect can be reduced 40%. This makes the patch far more acceptable to patients. Further, with some drugs, the irritation of the skin by the drug is proportional to the flux of drug from the patch. In these cases, the same sized patch would be used but the flux of drug from the patch would be reduced. This will in turn reduce the side-effects of skin irritation which may be associated with transdermal drug delivery.

Further illustrations of the dosage calculation of the present invention are provided in Table V, as described below.

TABLE V

| Drug | Ketorolac | Methadone | Tocainide | Warfarin | Nilvadipine | Flurbiprofen |
|---|---|---|---|---|---|---|
| Instant daily dose (racemate) (mg) | 200 | 50 | 1200 | 10 | 20 | 100 |
| Racemate half-life (hr) | 4 | 10 | 13.5 | 37 | 6 | 4 |
| Eudismic ratio | 230 | 30 | 3 | 5 | 100 | 20 |
| Instant daily dose (eutomer) (mg) | 100.4 | 25.8 | 800 | 6 | 10.1 | 52.5 |
| Transdermal dose of racemate, calculated from FIG. 2 (mg) | 50 | 25 | 768 | 10 | 6.8 | 24.7 |
| Transdermal dose of eutomer, per Equation 4 (mg) | 25.1 | 12.9 | 511 | 6 | 3.5 | 13.1 |
| Clearance ratio | 1.75 | 1.5 | 1.35 | 1.2 | 0.5 | .895 |
| Transdermal dose of eutomer using clearance ratio, per Equation 5 (mg) | 14.3 | 8.6 | 378 | 5 | 6.8 | 14.6 |

TABLE V-continued

| Drug | Ketorolac | Methadone | Tocainide | Warfarin | Nilvadipine | Flurbiprofen |
|---|---|---|---|---|---|---|
| Change in dose and change in patch size obtained by consideration of clearance ratio (%) | −43 | −33 | −35 | −17 | +100 | +11 |

The first row of Table V provides the typical daily (24 hour) instant dose for a particular drug. For example, methadone is administered orally at 50 mg per day, whereas ketorolac is administered intravenously at 200 mg per day. The second and third rows show the half life of the racemic mixture and the eudismic ratio, respectively.

Based on the daily instant dose and the eudismic ratio, the daily instant dose of the eutomer required to achieve the same effect is calculated according to Equation 3, at page 12 of the specification, and is represented in row 4. For example, for methadone:

$$D_E \times (a) = \frac{D_R}{2} \times (a + b),$$

and, given that a=30, b=1, $D_R$=50 mg, and $D_E$=25.8 mg.

The transdermal dose of the racemate which corresponds to the intravenous or oral dose of the racemate is calculated based on the half-life of the drug as described in Baker et al., and as exemplified in Table I and FIG. 2 herein. These data are described in row 5 of Table V.

The transdermal dose of the eutomer of the drug is given at row 6, which is derived using Equation 4. For example, for methadone:

$$\frac{D_E}{D_R} = 0.5 \left( 1 + \frac{1}{E.R.} \right) \times 100\%$$

when $D_R$=25, and E.R.=30, then $D_E$=12.9 mg. Similarly, for flurbiprofen, where $D_R$=52 and E.R.=20, then $D_E$=13.1 mg.

The clearance ratios for each drug are listed in row 7 of Table V. By incorporating the clearance ratios into the calculation for the transdermal dose of the eutomer, as provided in Equation 5, the transdermal dose according to the present invention is given in row 8. For example, for ketorolac, which has a clearance ratio of 1.75, the calculated eutomer transdermal dose according to the present invention is 14.3 mg, rather than the 25.2 mg obtained from Equation 4.

Similarly, methadone has a clearance ratio of 1.5. indicating that the racemate is removed from the body less rapidly than the eutomer. Thus, the required dosage of the eutomer of methadone is 8.6 mg, rather than the 12.9 mg calculated on the basis of Equation 4.

Drugs with clearance ratios of less than one, for example flurbiprofen and nilvadipine, require a higher dose of the eutomer than would be calculated according to Equation 4. For example, nilvadipine has a eudismic ratio of 100, and a clearance ratio of 0.5. The transdermal dose of the eutomer of nilvadipine according to the prior art calculation would be expected to be 3.5 mg (row 6). However, when the clearance ratio of the eutomer is taken into consideration, the dose required for administration is 6.8 mg. This corresponds to the dosage of the racemate that would be delivered transdermally. Therefore, although nilvadipine may initially appear to be a good candidate for the transdermal delivery of the eutomeric form (based in part on its high eudismic ratio), consideration of the clearance ratio according to the present invention indicates that no dosage benefit is obtained by the transdermal delivery of the eutomer rather than the racemate. Flurbiprofen similarly requires an increased dose of the eutomer when the clearance ratio is considered.

The reduction in dosage and corresponding reduction in patch size resulting from the methods of the present invention is shown in row 9 of Table V. For ketorolac, the dose of 14.3 mg is 57% of the transdermal dose of the active form when clearance ratio is not considered, and therefore a 43% reduction in dose is attained by the present invention. Further, the dose of ketorolac according to the present invention is 14% of the once-a-day dose of the active form (row 4), and 7% of the once-a-day dose (row 1) of the racemate. Similarly, methadone exhibits a 33% dose reduction over the calculation for the transdermal dose when clearance ratio is not considered. On the other hand, flurbiprofen and nilvadipine require an increased dosage (11% and 100% respectively) when clearance ratio is considered. That is, to maintain dosage efficacy for these drugs, more of the active form of the drug must be administered than previously thought.

Therefore it can be seen than the dosage for the transdermal delivery of eutomers of chiral drugs can be economically and therapeutically optimized when the eudismic ratio and clearance ratios are considered, indicating that some drugs are clearly better candidates for transdermal delivery than others.

In addition to the reduction in dosage that may be obtained by the methods of the present invention, a corresponding reduction in patch size results. For example, methadone has a skin permeability of 17 $\mu$g/cm$^2$/hour, which corresponds to 0.408 mg/cm$^2$/day. Thus, the administration of 8.6 mg of the eutomer of methadone according to the present invention would require a patch size with an active area of approximately 20 cm$^2$. If clearance ratio had not been considered, a 31 cm$^2$ patch would be required to deliver 12.9 mg of the methadone eutomer. Many patients consider this to be an unacceptably large patch size.

The absolute patch size for any particular eutomer depends on the patch configuration and design, and on the permeability of the drug. However, the relative patch sizes are related to the amount of drug to be delivered. Therefore, the % reduction in dosage in table 9 corresponds to a % reduction in patch size.

Thus the applicants have discovered that if transdermal delivery of eutomers is to be considered as a way of reducing the expected size of a transdermal patch, the eudismic ratio and the clearance ratio of the drug should be considered. The best results, i.e., smaller doses of the drug, and a corresponding smaller patch size, are obtained when both the eudismic ratio and the clearance ratio are greater than 1. Preferably the eudismic ratio is greater than 2, and more preferably greater than 10. Most preferably, the clearance ratio is greater than 1.2 and the eudismic ratio is greater than 10.

The preferred method of separating the eutomer of a chiral drug from a racemic mixture will be dependent upon the drug of interest. Various methodologies for optical resolution are available in the art [see *Kirk-Othmer Encyclopedia of Chemical Technology*, 3d Ed. pp. 325–327 (1982), incorporated herein by reference]. Optical resolution can be obtained by direct crystallization of racemic mixtures but, generally, resolution involves formation of diastereomer derivatives by means of an optically active resolving agent. Unlike enantiomers, diastereomers have different physical properties and may be separated by a variety of methods such as fractional crystallization, gas-liquid chromatography, thin layer chromatography, and liquid chromatography.

Direct resolution of enantiomers can be achieved by liquid chromatographic techniques involving the use of optically active packing materials.

Once the desired eutomer having a clearance value greater than its corresponding distomer is obtained, a method of transdermal delivery is selected. The drug may be applied directly to the skin using any of the vehicles for drug delivery known in the pharmaceutical arts, such as creams, lotions, ointments, gels or pastes. In these embodiments, the skin acts as a rate controlling membrane for the delivery of the drug. Alternatively, the vehicle for drug delivery may be a bandage or skin patch, incorporating a drug/enhancer depot and preferably some means for controlling the flux of enhancer and/or drug from the patch.

Transdermal drug delivery involves the permeation of the drug through a patient's skin. The stratum corneum, a thin layer of dense, highly keratinized cells, is the primary obstacle in drug permeation. In order to increase permeability of the stratum corneum, permeation enhancers are often employed. Thus, the pharmaceutical compositions of the present invention comprise a eutomer of a chiral drug and may also comprise one or more skin permeation enhancers.

Various compounds for enhancing the permeability of skin are known in the art. U.S. Pat. Nos. 4,006,218, 3,551, 554 and 3,472,931, for example, respectively describe the use of dimethylsulfoxide (DMSO), dimethyl formamide (DMF) and N,N-dimethylacetamide (DMA) to enhance the absorption of pharmacologically active agents through the stratum corneum. Other compounds which have been used to enhance skin permeability include decylmethylsulfoxide, diethylene glycol monoethyl ether, polyethylene glycol monolaurate (U.S. Pat. No. 4,568,343), glycerol monolaurate (U.S. Pat. No. 4,746,515) ethanol (U.S. Pat. No. 4,379, 454), eucalyptol (U.S. Pat. No. 4,440,777), and lecithin (U.S. Pat. No. 4,783,450).

One type of vehicle is a reservoir-type transdermal patch, such as that taught in U.S. Pat. No. 4,379,454, incorporated herein by reference.

Another embodiment of the pharmaceutical compositions of the present invention is a skin patch comprising an impermeable backing layer and a matrix layer that contains the eutomer and an enhancer. The matrix layer may be a microporous material impregnated with solvent enhancer and dissolved eutomer. A variety of polymers that might be used as a microporous matrix are known in the art. Typically, a microporous polypropylene, such as Celgard, obtainable from Celanese Corp., Charlotte, N.C., might be used.

Alternatively, a monolithic system can be used in which a non-porous matrix is swollen with dissolved enhancer and a eutomer. The choice of monolithic carrier depends on the enhancer material. Materials which might be used are, for example, acrylate and methylate copolymers. Monomers of these materials such as hydroxy ethyl methacrylate dissolved in a mixture of drug and enhancer can be polymerized by a suitable free radical polymerization reaction to yield a cross-linked gel containing drug and enhancer. By varying the concentration of the cross-linking agent or the chemistry and concentration of the monomer the density of the gel is increased. Dense gels prepared from high concentrations of monomers and high concentrations of cross-linked agents release the enhancer more slowly than less dense gels. The chemistry of these reactions and the monomers and cross-linked agents that can be used are discussed on pages 179–184 in Baker, supra.

The patch embodiments described above may be held in contact with the skin in a variety of ways, such as by means of a porous or non-porous overlay coated wholly or partly with adhesive, by an adhesive layer between the patch nd the skin, or by an annulus of adhesive around the periphery of the patch. Representative adhesives used for transdermal patches include: acrylic-based pressure-sensitive adhesives manufactured by many companies including 3M and Avery; polyisobutylene with blends of low and high molecular weight polymers (Exxon, Vistanex); and silicone-based adhesives manufactured by Dow Corning (355 and BioPSA). Other variations in the basic geometries described, to assist for example, in retaining good skin contact or an occlusive environment are also intended to be within the scope of the invention.

The invention is now further illustrated by Examples 1–14 which are exemplary but not scope-limiting.

RESOLUTION OF CHIRAL DRUGS

EXAMPLE 1

Resolution of 5-benzoyl-1, 2-dihydro-3H-pyrrolo-[1,2-a]-pyrrole-1-carboxylic acid (Ketorolac Acid)

a) Preparation of the (−)-cinchonidinium salt of ketorolac

A solution of 48.08 g (0.16 mol) of cinchonidine in 800 ml of hot ethanol was added to a solution of 48.85 g (0.16 mol) of (+/−)-ketorolac in 200 ml of ethyl acetate. The resulting solution was heated at reflux temperature for 0.5 hr, the solvents were removed in vacuo, and the residue was crystallized from a mixture of 1600 ml of ethyl acetate and 650 ml of ethanol. After separation by filtration of 12.5 g of insoluble matter from the boiling mixture, the solution was cooled at room temperature. The crystallized salt was collected by refiltration, and air-dried at 45°–50° C. to yield 20.9 g (47%) of the title compound, m.p.204°–206° C.; $[\alpha]_D = -227°$ (c1, MEOH).

b) Preparation of (−) ketorolac 106 ml of 2N sulfuric acid was added to a stirred suspension of 19.8 g (0.036 mol) of the above cinchonidinium salt in 2121 ml of water. The mixture was extracted with ethyl acetate (400 ml) and the extract was washed with water, dried over anhydrous $CaCl_2$ and evaporated in vacuo. The crude acid was crystallized from a mixture of 140 ml of ethyl acetate and 80 ml of hexane to give 7.77 g (86%) of pure (−)-ketorolac, m.p. 172°–174° C.; $[\alpha]_D = -175°$ (c1, MeOH).

EXAMPLE 2

Permeability of Racemic Ketorolac Tromethamine

A 32% solution of racemic ketorolac tromethamine in 33 wt % isopropyl alcohol, 33 wt % water, 1.2 wt % isopropyl myristate was prepared. The mixture was gelled with 0.4 wt % hydroxypropyl-cellulose.

Figure 3:
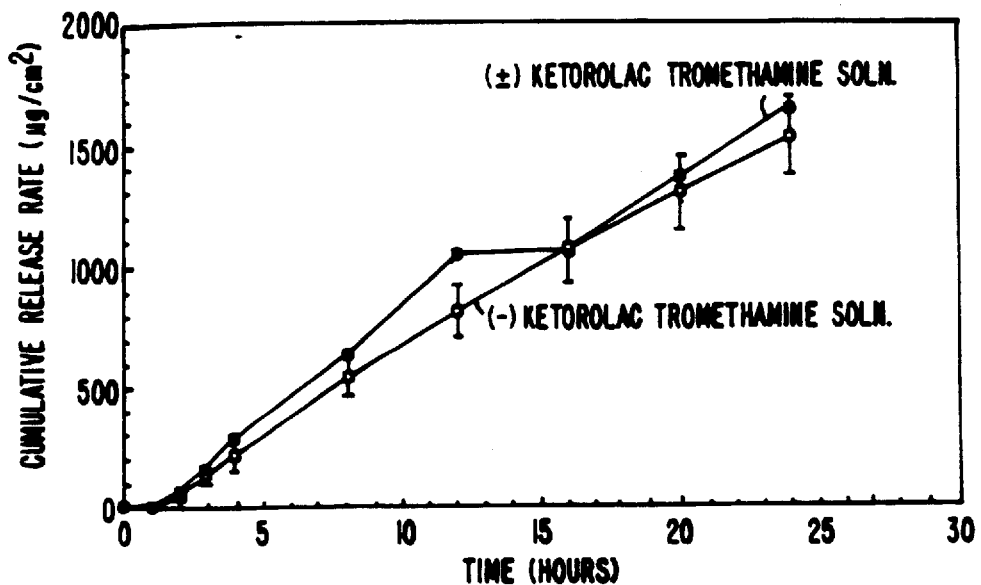
FIG. 3 compares the cumulative release rates of racemic ketorolac tromethamine and ketorolac tromethamine through human skin.

The in vitro human skin permeation rates were measured using flow-through diffusion cells (LGA) maintained at 32° C. The receptor fluid, isotonic saline, was pumped into and through the cells by a peristaltic pump. Samples were collected in glass vials arranged in an automatic fraction collector. The human skin was placed on the lower half of the diffusion cell with the stratum corneum facing the donor compartment. The test solution was placed on the stratum corneum and the amount of racemic ketorolac tromethamine permeated across the skin ($\mu g/cm^2$) was determined by assaying the samples collected by HPLC. The cumulative release of racemic ketorolac tromethamine versus time profile is shown in FIG. 3.

EXAMPLE 3

Permeability of S(–) Ketorolac Tromethamine

A solution was prepared and tested according to Example 2 except that the drug was the S(–) enantiomer of ketorolac tromethamine. The cumulative release of S(–) ketorolac tromethamine v. time profile is shown in FIG. 3.

EXAMPLE 4

Permeability of Racemic Ketorolac

Figure 4:
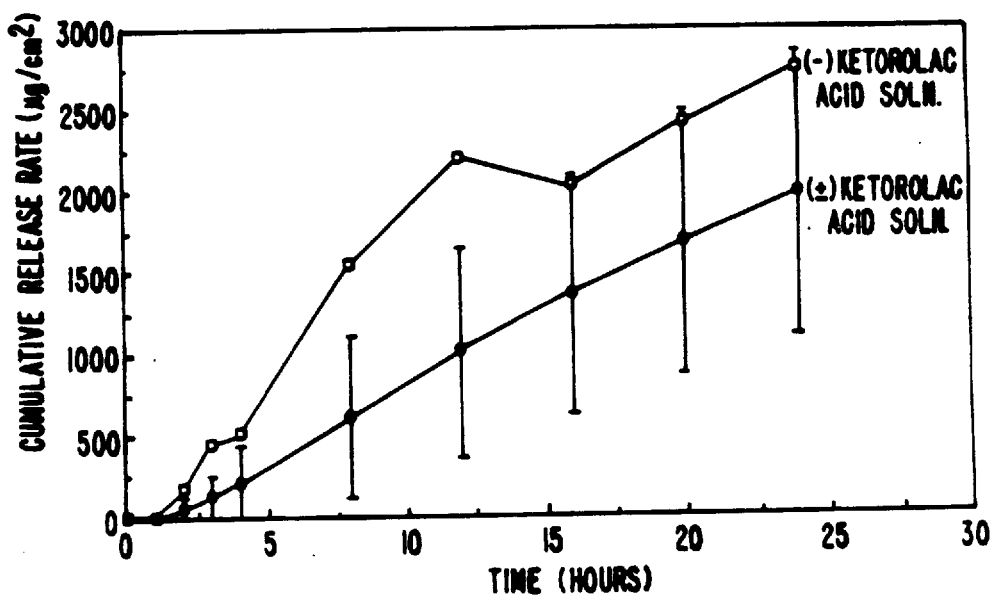
FIG. 4 compares the cumulative release rates of racemic ketorolac acid and (−) ketorolac acid through human skin.

A 6.3 wt % solution of racemic ketorolac in 44 wt % isopropyl alcohol, 48 wt % water, 1.4 wt % isopropyl myristate was prepared. The mixture was gelled with 0.45 wt % hydroxypropyl-cellulose. The release of racemic ketorolac acid through human skin was measured as outlined in Example 2 and is shown in FIG. 4.

EXAMPLE 5

Permeability of S(–) Ketorolac

A 7.2 wt % solution of (–) ketorolac acid in 49 wt % isopropyl alcohol, 41 wt % water, 1.9 wt % isopropyl myristate was prepared. The mixture was gelled with 0.45 wt % hydroxypropyl-cellulose. The release of S(–) ketorolac acid through human skin was measured as outlined above and is shown in FIG. 4.

Examples 2–5 show that the permeability through the skin of the eutomer of ketorolac is approximately the same as the racemic form at 62–83 $\mu g/cm^2/hr$ which corresponds to 1.5–2.0 $mg/cm^2/day$. Based on the calculations disclosed above, the use of the eutomer means a patch with an area of approximately 10 $cm^2$ should be able to deliver levels of ketorolac therapeutically effective to an injection of 200 mg delivered once a day.

EXAMPLE 6

Permeability of Racemic Methadone Free Base

Methadone free base was prepared from the hydrochloride salt. A known mass of methadone hydrochloride was dissolved in a minimal volume of distilled water. An equimolar amount of 0.5N sodium hydroxide was added drop-wise. The solution was adjusted to pH 7–8 by the addition of sodium hydroxide until a slight excess of base was present. The solution was transferred to a separatory funnel, and the free base extracted into petroleum ether. The aqueous phase was then removed and the petroleum either phase dried over anhydrous sodium sulfate. Exposure to light and air was minimized when handling the free base. The solution was filtered and the ether removed by vacuum evacuation or gentle boiling to yield white crystals. The purity of the crystals was checked by melting point measurement. The process was repeated a number of times with an average methadone free base yield of 80–90%.

Skin samples were obtained from refrigerated cadavers, excised to a thickness of 250 microns using a dermatome, and tested for methadone free base/enhancer permeability at 30° C., the temperature of functioning skin.

Figure 5:
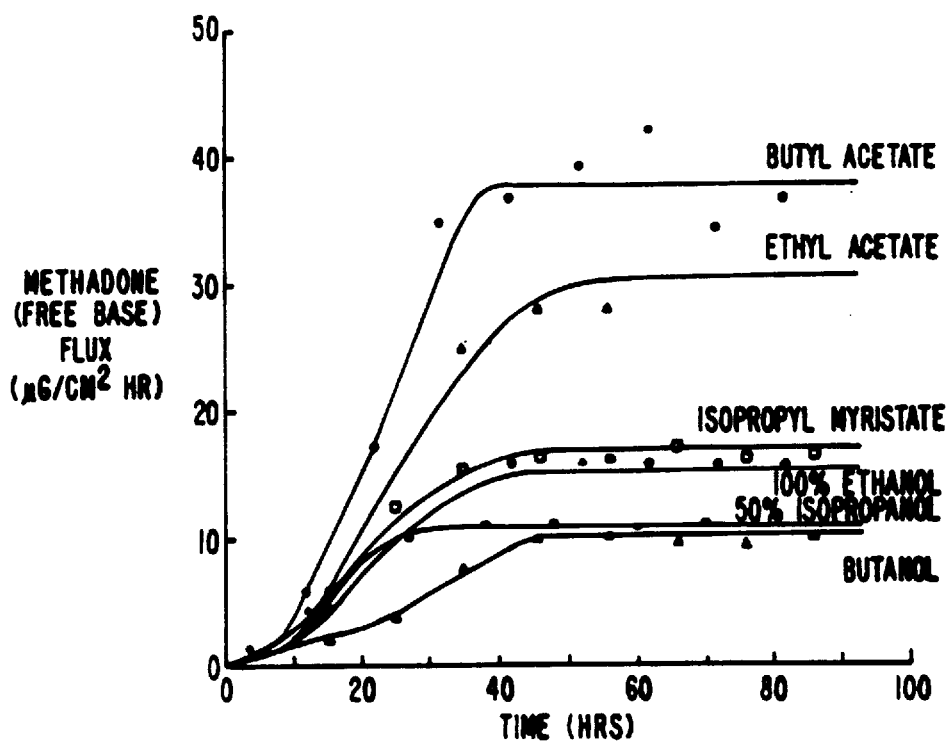
FIG. 5 shows the flux of methadone free base in isopropyl myristate.

The samples were mounted in a Teflon® flow-through diffusion cell with the permeate collected in a time-programmed fraction collector which allows samples of the receiving phase to be taken at any desired interval. Air bubbles present inside the Teflon® cells on the receiving phase side can decrease the total membrane area, so bubble traps were incorporated into the system to eliminate this. Isotonic saline was passed through the diffusion cell to serve as a receiving phase. This phase contacted the skin samples on the side away from the stratum corneum. The exposed area of the skin was 0.32 $cm^2$. Skin permeability was measured by the rate of permeation of drug into the receiving phase. Using this testing procedure, a saturated solution of methadone free base in isopropyl myristate resulted in a flux of 17 $\mu g/cm^2$ hr as shown in FIG. 5.

EXAMPLE 7

Permeability of Racemic R(–) Methadone Free Base

The R(–) enantiomer of methadone is separated using procedures known in the art. R(–) methadone free base is prepared according to Example 4 except that the R(–) enantiomer of methadone is used. Skin permeability is tested using the procedures of Example 4 and is shown to be essentially equivalent to that of the racemic mixture.

EXAMPLE 8

Racemic Ketorolac Tromethamine Transdermal Patch

Transdermal systems were fabricated as follows. A pressure sensitive adhesive was prepared by casting an acrylic adhesive solution onto a siliconized polyethylene teraphythalate (3M #1033) with a 750 micron knife. The solvent was evaporated in a 95° C. forced air oven for minutes. The resultant film, 75 microns thick, was laminated to another polyester film (3M Cotran 9710). This three layer assembly was peripherally heat sealed to aluminized polyester backing (3M Scotchpak® 1006) forming delivery devices with an active releasing area of 17 $cm^2$. A 32% solution of racemic ketorolac tromethamine in 33 wt % isopropyl alcohol, 33 wt % water, 1.2 wt % isopropyl myristate was prepared. The solution was gelled with 0.4 wt % hydroxypropyl-cellulose. The reservoir of the patch was filled with the gelled racemic ketorolac tromethamine solution through a small opening left in the heat seal.

This opening was sealed closed after filling. The anti-inflammatory and analgesic activities of the drug are determined by using the carrageenan rat paw edema and mouse phenylquinone writhing assays.

EXAMPLE 9

S(–) Ketorolac Transdermal Patch

A patch is prepared according to the procedure set forth in Example 5 except that the drug is the S(–) enantiomer of ketorolac tromethamine and the active releasing area of the patch is 11 $cm^2$. The anti-inflammatory and analgesic activities of the drug are determined by using the carrageenan rat paw edema and mouse phenylquinone writhing assays.

EXAMPLE 10

Racemic and R(–) Methadone Free Base Transdermal Patches

Racemic and R(–) methadone transdermal systems are fabricated using the procedures described in Example 8 except that the drugs used are methadone free base and R(-) methadone free base, respectively. The normal oral dose of racemic methadone is 50 mg/day. Delivered transdermally, 25 mgs/day of racemic methadone is effective. Based on the eudismic ratio of for methadone, the calculated transdermal dose of the R(-) form according to Equation 4 is:

$$\frac{D_E}{25} = 0.5 \left(1 + \frac{1}{30}\right) \times 100\% = 12.9 \text{ mg/day}$$

However, when the clearance ratio is taken in account according to the teachings of the present invention, the amount of R(-) methadone to be delivered transdermally is calculated according to Equation 5:

$$\frac{D_E}{25} = 0.5 \left(1 + \frac{1}{30}\right) \left(\frac{100\%}{1.5}\right) = 8.6 \text{ mg/day}$$

Thus, the transdermal dose of R(-) methadone required for an equivalent biological effect as a 50 mg/day conventional dose of the racemic form of methadone is 8.6 mg/day. This dose corresponds to a 21.5 cm² patch size for R(-) methadone.

EXAMPLE 11

Preparation of Ketorolac Matrix Patch

To prepare the matrix, 0.2 g of (-) ketorolac acid is dissolved in 0.5 g of polyethylene glycol 200, 0.25 g of propylene glycol and 0.05 g of polysorbate 80, whereby a solution is formed. This solution is added to 10 g of polymer solution (Monsanto GELVAR® 737) and then mixed for 20–30 min. After mixing, the mixture is settled for about 20 minutes to remove air bubbles and is cast onto the backing material (3M Scotchpak® 1006 or 1021). The cast mixture is dried for 30 min. at 45° C. To make a triple layers matrix, the 2nd and 3rd layers are sequentially cast over the prior layer after the prior layer is settled and dried. This formation is then cut into appropriate patch sizes.

EXAMPLE 12

Preparation of Ketorolac Monolithic Patch

Monolithic patches of ketorolac are made as follows. A solution of (-) ketorolac acid-loaded Pellethane 2363-80AE is made by mixing Pellethane pellets into tetrahydrofuran, adding 10% (-) ketorolac and agitating on a bottle roller. A layer of material grade 3M-1005 backing is spread in a petri dish and covered with the matrix mixture. The petri dish is covered and the matrix is left for the solvent to evaporate at room temperature. Patches with an area of 3.88 cm² are cut from the finished matrix with a punch. Device release-rate measurements are made by suspending the test device in a wire cage in an isotonic saline solution under constant agitation by a magnetic stirrer at 30°. Periodic saline samples are taken for HPLC analysis using a Novapak 8 C 150×4.6 mm 5μ.

EXAMPLE 13

Preparation of Ketorolac Mixed Monolith/membrane Patch

Monoliths containing 50% ketorolac are made by the same general procedure as described in Example 3. Several different compositions can be made:

A. A membrane of 100 μm thick Sclairfilm® HD-2-PA is cast onto the monolith.
B. A 38 μm thick membrane of polyethylene grade HD-106 obtained from Consolidated Thermoplastics is cast onto the monolith.
C. The membranes of examples A and B are coated with 25-μm thick layer of BIO PSA grade X7-2920.
D. The monolith is coated with polyethylene, double-sided medical adhesive tape grade 3M-1509.
E. The monolith is coated with polyethylene, doublesided, medical adhesive tape grade 3M-1512.

EXAMPLE 14

Preparation of Ketorolac Reservoir

A microporous polyethylene film (3M Cotran 9710) is heat sealed to a polyester backing layer (3M Scotchpak® 1009). A layer of adhesive including 10% IPM in an acrylate adhesive is cast onto the polyethylene film and covered with a release liner. The pouch formed between the polyester film and the polyethylene film is filled with a gelled solution of (-) ketorolac tromethamine. Examples of gelled solutions are:

|  | A | B | C | D |
|---|---|---|---|---|
| (-) Ketorolac tromethamine | 5% | 10% | 15% | 20% |
| Carbomer | 1% | 1.5% | 1% | 0.5% |
| Alcohol | 20% | 30% | 10% | 50% |
| EDTA | — | — | — | 0.1% |
| BHT | 0.1% | — | 0.5% | — |
| Purified water, q.s. to | 100% | 100% | 100% | 100% |

After heat sealing, the patches are cut to have an active area of 25 cm². The patches are packaged in a Barex pouch.

EXAMPLE 15

Preparation of Ketorolac Carbomer Gel (-) Ketorolac tromethamine is dissolved in purified water (about ⅓ of total amount to be prepared). The pH is adjusted to 7.3±0.1 using NaOH 10% (W/W) solution or trolamine. Alcohol is mixed with ⅔ of the total amount of water and then carbomer is added while stirring. The carbomer is allowed to fully swell for 1 hour at 50° under constant stirring. The remaining NaOH or trolamine is added and stirred for 15 minutes. The ketorolac solution is joined with the carbomer gel under vacuum and stirred well. The pH is adjusted, if necessary, to between 7.3 and 7.5 with NaOH 10% (w/w) solution or trolamine. The remaining purified water is added and stirred for 15 minutes. The gel is collected in a suitable container and introduced into tubes. The gels have the following composition:

|  | A | B |
|---|---|---|
| (-) Ketorolac tromethamine | 2% | 2% |
| Carbomer | 1.2% | 1.2% |
| Alcohol | 20% | 20% |
| NaOH 5% w/w sol. | 5% | — |
| Trolamine | — | 1.94% |
| Purified water q.s. to | 100% | 100% |

EXAMPLE 16

Preparation of Ketorolac Hydroxyethylcellulose Gel (-) Ketorolac tromethamine is dissolved in purified water (about ⅓ of total amount to be prepared). The pH is adjusted to 7.3±0.1 using 1N NaOH. Alcohol is mixed with ⅔ of the total amount of water and then hydroxyethylcellulose is added while stirring. The hydroxyethylcellulose is allowed to fully swell for 1 hour at 50° under constant stirring. The remaining NaOH is added and stirred for 15 minutes. The ketorolac solution is joined with the hydroxyethylcellulose gel under vacuum and stirred well. The pH is adjusted, if necessary to between 7.3 and 7.5 with NaOH. The remaining purified water is added and stirred for 15 minutes. The gel is collected in a suitable container and introduced into tubes. When present, sodium edetate has been solubilized together with ketorolac. The gels have the following composition:

|  | A | B |
| --- | --- | --- |
| (−) Ketorolac tromethamine | 1% | 1% |
| Hydroxyethylcellulose | 2% | 2% |
| Alcohol | 20% | 20% |
| NaOH 1N sol. | — | 1.15% |
| Sodium edetate | — | 0.5% |
| Purified water q.s. to | 100% | 100% |

The foregoing description of the preferred embodiments of the present invention has been presented for purposes of illustration and description. They are not intended to be exhaustive or to limit the invention to the precise form disclosed, and many modifications and variations are possible in light of the above teaching.

All publications and patent applications herein are incorporated by reference to the same extent as if each individual publication or patent application was specifically and individually indicated to be incorporated by reference.

Such modifications and variations which may be apparent to a person skilled in the art are intended to be within the scope of this invention.

What is claimed is:

1. A pharmaceutical composition for the transdermal delivery of S(−) ketorolac, thereby providing an injectable equivalent of about 200 mg/day of racemic ketorolac comprising:
   S(−) ketorolac initially present in a daily dosage amount of about 14.3 mg substantially free of the distomer of ketorolac; and
   a vehicle for transdermal delivery of the eutomer.

2. A pharmaceutical composition for the transdermal delivery of R(−) methadone, thereby providing an injectable equivalent of about 50 mg/day of racemic methadone comprising:
   R(−) methadone initially present in a daily dosage amount of about 8.6 mg substantially free of the distomer of methadone; and
   a vehicle for transdermal delivery of the eutomer.

3. A pharmaceutical composition for the transdermal delivery of R(−) tocainide, thereby providing an injectable equivalent of about 1200 mg/day of racemic tocainide comprising:
   R(−) tocainide initially present in a daily dosage amount of about 378 mg substantially free of the distomer of tocainide; and
   a vehicle for transdermal delivery of the eutomer.

4. A pharmaceutical composition for the transdermal delivery of S(−) warfarin, thereby providing an injectable equivalent of about 10 mg/day of racemic warfarin comprising:
   S(−) warfarin initially present in a daily dosage amount of about 5 mg substantially free of the distomer of warfarin; and
   a vehicle for transdermal delivery of the eutomer.

5. A method for providing an injectable equivalent of about 200 mg/day of racemic ketorolac, comprising the step of
   applying transdermally the pharmaceutical composition of claim 1.

6. A method for providing an injectable equivalent of about 50 mg/day of racemic methadone, comprising the step of
   applying transdermally the pharmaceutical composition of claim 2.

7. A method for providing an injectable equivalent of about 1200 mg/day of racemic tocainide comprising the step of
   applying transdermally the pharmaceutical composition of claim 3.

8. A method for providing an injectable equivalent of about 10 mg/day of racemic warfarin comprising the step of
   applying transdermally the pharmaceutical composition of claim 4.

* * * * *